United States Patent
Tapocik

(10) Patent No.: US 11,224,411 B1
(45) Date of Patent: Jan. 18, 2022

(54) NASOPHARYNGEAL COLLECTION SWAB WITH PREDETERMINED DECOUPLING POINT

(71) Applicant: Bryan Tapocik, Highland, CA (US)

(72) Inventor: Bryan Tapocik, Highland, CA (US)

(73) Assignee: Innovative Product Brands, Inc., Highland, CA (US)

( * ) Notice: Subject to any disclaimer, the term of this patent is extended or adjusted under 35 U.S.C. 154(b) by 0 days.

(21) Appl. No.: 17/117,806

(22) Filed: Dec. 10, 2020

Related U.S. Application Data

(60) Provisional application No. 63/078,083, filed on Sep. 14, 2020.

(51) Int. Cl.
 *A61B 10/00* (2006.01)
 *A61F 13/38* (2006.01)

(52) U.S. Cl.
 CPC .......... *A61B 10/0051* (2013.01); *A61F 13/38* (2013.01); *A61B 10/0096* (2013.01)

(58) Field of Classification Search
 None
 See application file for complete search history.

(56) References Cited

U.S. PATENT DOCUMENTS

| | | | | |
|---|---|---|---|---|
| 2,835,246 A | * | 5/1958 | Boettger | A61B 10/0096 600/570 |
| 4,175,008 A | * | 11/1979 | White | A61B 10/0096 206/15.2 |
| 4,311,792 A | * | 1/1982 | Avery | C12M 45/22 15/144.4 |
| 5,623,942 A | * | 4/1997 | Pestes | A61B 10/02 600/562 |
| D614,292 S | | 4/2010 | Anderson | |
| 10,517,575 B2 | | 12/2019 | Triva | |
| 2004/0014237 A1 | * | 1/2004 | Sugiyama | A61B 10/0096 436/174 |
| 2015/0127093 A1 | * | 5/2015 | Hosmer | A61F 2/2427 623/2.11 |

(Continued)

FOREIGN PATENT DOCUMENTS

WO WO9731675 8/2017

OTHER PUBLICATIONS

Petruzzi G, De Virgilio A, Pichi B, et al. COVID-19: Nasal and oropharyngeal swab. Head & Neck. 2020; 42: 1303-1304. https://doi.org/10.1002/hed.26212 (published online on Apr. 30, 2020). (Year: 2020).*

*Primary Examiner* — Matthew Kremer
(74) *Attorney, Agent, or Firm* — Minta Law Group LC

(57) ABSTRACT

The described nasopharyngeal or nasal swabs allow for collection of biological specimens. In an illustrative embodiment, a first member may be coupled to a second member to form the nasopharyngeal swab. The first member may include a male connector and a collection end. The second member may incorporate a corresponding female connector and a handle. The first member may be decoupled from the second member when force is applied to the swab causing it to bend beyond a threshold arc. The force may be applied to a proximal position on the first member through a container. The first member having the collection end may be gathered in the container after decoupled from the second member.

7 Claims, 7 Drawing Sheets

(56) References Cited

U.S. PATENT DOCUMENTS

| | | | |
|---|---|---|---|
| 2015/0230872 A1* | 8/2015 | Lundkvist | A61B 10/0291 600/572 |
| 2016/0038348 A1* | 2/2016 | Booth | A46B 15/0081 433/136 |
| 2017/0074316 A1* | 3/2017 | Kim | A61F 5/0125 |
| 2021/0038200 A1* | 2/2021 | Wisherd | G01N 1/08 |

* cited by examiner

NASOPHARYNGEAL COLLECTION SWAB WITH PREDETERMINED DECOUPLING POINT

RELATED DISCLOSURE

This disclosure claims priority to Provisional Application Ser. No. 62/078,083 filed on Sep. 14, 2020 titled Device Allowing Collection of Biological Specimens and Method Thereof, which is hereby incorporated by reference in its entirety.

TECHNICAL FIELD

The present disclosure relates to medical devices and more particularly, to a swab allowing for collection of biological specimens that may be easily stored into a container for subsequent testing.

BACKGROUND

Over six million cases of coronavirus disease 2019, otherwise known as COVID-19, have been identified in the United States resulting in over one hundred and ninety thousand deaths. Respiratory tract diseases, including COVID-19, may affect patients of all ages, although often it is more serious in the very young and the very old. In order to be effective in treating such infectious disorders, testing should be timely made.

Devices, such as nasopharyngeal or nasal swabs, for collecting biological specimens of organic material may be used for testing. Generally, these devices may include a cylindrical rod or stick containing a collection end or tip. Material on the collection end may include rayon or a natural fiber such as cotton with hydrophilic properties to allow rapid absorption of a quantity of specimen to be collected and tested. Stable adherence of the fiber wrapped around the end or tip of the rod or stick may generally be achieved by gluing.

Typically, the swab may be inserted into the nasal septum, just above the floor of the nasal passage, to a nasopharynx of the patient, until resistance is felt. The swab may be inserted from nostrils of the patient to a point coinciding with an outer opening of their ear. The swab may be kept in place for several seconds to absorb secretions. The swab may then slowly be removed while rotating it. A collection tube may be opened and the swab inserted therein. The swab may be broken at a groove with the remaining portion of the swab discarded.

This break however may occur at different locations on the swab leading to varying sizes of collected specimens. These may be hard to process or evaluate in large quantities. Furthermore, current swabs come in a single piece requiring packaging of greater length. These swabs are structurally elongated leading to potential snaps during transit. The present disclosure provides for a device allowing collection of biological specimens and method thereof that addresses the above identified concerns. Controlling a breakage point allowing for uniform specimens will be shown. Other benefits and advantages will become clear from the disclosure provided herein and those advantages provided are for illustration. The statements in this section merely provide the background related to the present disclosure and does not constitute prior art.

SUMMARY

This summary is provided to introduce a selection of concepts in a simplified form that are further described below in the DESCRIPTION OF THE DISCLOSURE. This summary is not intended to identify key features of the claimed subject matter, nor is it intended to be used as an aid in determining the scope of the claimed subject matter.

According to one aspect of the present disclosure, a swab is provided. The swab may include a first member having a collection end and a second member having a handle. The first member and second member may be coupled together at a connection point with the first member and second member becoming decoupled when the first member and second member are bent beyond a threshold arc.

According to another aspect of the present disclosure, a nasal swab constructed to collect and release a biological sample is provided. The nasal swab may include a first member having a collection end at a distal portion and a male connector at a proximal portion. In addition, the nasal swab may include a second member having a handle at a proximal portion and a female connector at a distal portion coupled with the male connector of the first member. The first member and second member may become decoupled when a force is applied on the first member at or near its proximal portion.

According to yet another aspect of the present disclosure, a method of collecting and releasing biological specimens is provided. The method may include coupling a first member with a second member to form a nasopharyngeal swab, positioning a patient with his or her face pointing upwards, inserting the nasopharyngeal swab through a nasal cavity of the patient, removing the nasopharyngeal swab from the patient, and bending the nasopharyngeal swab beyond a threshold arc to decouple the first member and second member.

BRIEF DESCRIPTION OF THE DRAWINGS

The novel features believed to be characteristic of the disclosure are set forth in the appended claims. In the descriptions that follow, like parts are marked throughout the specification and drawings with the same numerals, respectively. The drawing FIGURES are not necessarily drawn to scale and certain FIGURES may be shown in exaggerated or generalized form in the interest of clarity and conciseness. The disclosure itself, however, as well as a preferred mode of use, further objectives and advantages thereof, will be best understood by reference to the following detailed description of illustrative embodiments when read in conjunction with the accompanying drawings, wherein:

DESCRIPTION OF THE DISCLOSURE

The description set forth below in connection with the appended drawings is intended as a description of exemplary embodiments of the disclosure and is not intended to represent the only forms in which the present disclosure may be constructed and/or utilized. The description sets forth the functions and the sequence of blocks for constructing and operating the disclosure in connection with the illustrated embodiments. It is to be understood, however, that the same or equivalent functions and sequences may be accomplished by different embodiments that are also intended to be encompassed within the spirit and scope of this disclosure.

The present disclosure relates to medical devices. More particularly, this disclosure describes nasopharyngeal or nasal swabs allowing for collection of biological specimens. In an illustrative embodiment, a first member may be coupled to a second member to form the nasopharyngeal swab. The first member may include a male connector and a collection end. The second member may incorporate a corresponding female connector and a handle. The first member may be decoupled from the second member when force is applied to the swab causing it to bend beyond a threshold arc. The force may be applied to a proximal position on the first member through a container. The first member having the collection end may be gathered in the container after decoupled from the second member.

Numerous other modifications or configurations to the nasopharyngeal swab will become apparent from the description provided below. For example, the first member may include a female connector while the second member may include a male connector. Advantageously, the swab when being shipped in two distinct pieces may come in smaller packaging lengthwise. This may cause the swab to be more durable during shipment. Furthermore, and by having the members decouple after a force is applied to the swab, a predictable swab sample may be provided. That is, each sample may have a defined length allowing for uniform containers to store the samples. Other benefits and advantages will become clear from the disclosure provided herein and those advantages provided are for illustration.

Figure 1:
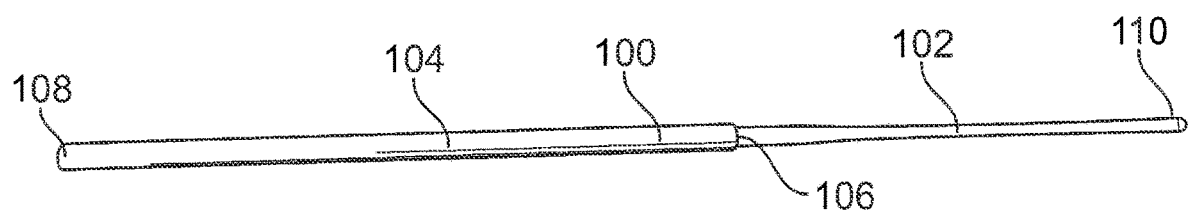
FIG. 1 is a schematic representation of an illustrative nasopharyngeal swab having multiple members affixed together in accordance with one aspect of the present disclosure.

Turning to FIG. 1, a schematic representation of an illustrative nasopharyngeal swab 100 having multiple members 102 and 104 affixed together in accordance with one aspect of the present disclosure is provided. The nasopharyngeal swab 100 may be made of plastic. Other materials may include chrome or stainless steel wire. Paper, wood, or other similar materials may be used to construct the members 102 and 104. The members 102 and 104 may be made of different materials from one another, for example, one member may be made of paper while the other may be constructed out of wood.

As shown, the nasopharyngeal swab 100 may include a first member 102 and a second member 104. The members 102 and 104 may be coupled to one another at a connection point 106. This coupling may be separated when force, such as lateral force, is applied to the swab 100 causing the first member 102 to be separated from the second member 104. An arc between the members 102 and 104 may be generated by the force causing them to be separated when a threshold arc is achieved. The force placement, which will be shown below, may occur at a proximal end of the first member 102.

The nasopharyngeal swab 100 may include a proximal end 108. This end 108 may be closer to a practitioner who is using the swab 100 on a patient. A distal end 110 of the nasopharyngeal swab 100 may include an absorbing material to collect biological specimens from the patient. This material may include polyester, or flocked nylon. The material used may coincide with a particular diagnostic application that may vary based on the test type.

Figure 2:
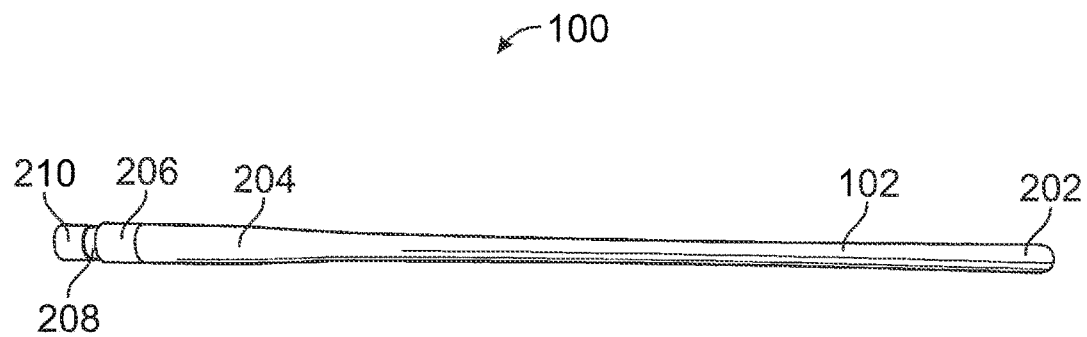
FIG. 2 is a schematic representation of an exemplary first member of the illustrative nasopharyngeal swab in accordance with one aspect of the present disclosure.

FIG. 2 is a schematic representation of an exemplary first member 102 of the illustrative nasopharyngeal swab 100 in accordance with one aspect of the present disclosure. The first member 102, for example, may be an elongated tubular structure. The structure may be made of materials which were discussed above. The first member 102 may have a smaller cross sectional area at a distal end leading to a larger cross sectional area at a proximal end.

The first member 102 may include a collection end 202 used for acquiring biological specimens. The materials may vary at the collection end 202. In one example, cotton may be used at the collection end 202. The cotton may provide an absorbent, soft, low cost, and safe solution for collecting specimens.

Rayon tipped swabs 100 may provide benefits over cotton swabs 100. The rayon may be located at the collection end 202. Rayon may be predictably soft and an economical choice where cotton is not suitable. In one example, rayon may be a synthetic spun fiber manufactured from wood pulp.

Polyester may be used for the collection end 202 of the swab 100. Polyester may be a synthetic spun fiber made from a polymer. Polyester has been tested and validated for use in specimen collection. In one example, rapid test diagnostics and PCR analysis may be implemented by using polyester.

In another example, polyurethane foam may be at the collection end 202, The foam may be produced in a range of porosities in sheet form. A common configuration for use in tipped applications is one hundred (100) pores per inch.

The first member 102 may have a smaller cross sectional area at the distal end which may be increased at a first section 204. Connected to the first section 204 may be a coupling structure, which allows the first member 102 to be joined to the second member 104. The first section 204 may include a large surface for which force may be applied to disconnect the first member 102 from the second member 104, as will be shown below.

For illustrative purposes, the coupling structure may include a second section 206, a groove 208, and a male connector 210. It should be noted that various configurations may exist and should not be limited to that shown for the coupling structure. For example, multiple grooves and varying diameters of cross sections may be used. As another example, the female connector may exist on the first member 102, instead of the male connector 210.

The second section 206 may have a larger cross sectional than that of the first section 204. When the first member 102 is inserted into the second member 104, the second section 206 of the first member 102 may be used such that the second member 104 does not overlap or extend past the second section 206.

Following the second section 206 and towards the proximal end of the first member 102, the groove 208 may be provided. The groove 208 may fit into the second member 104 when coupled to the first member 102. Advantageously, the groove allows for flexibility in the first member 102. That is, the flexibility may allow the swab 100 to bend but not break. Decoupling may result only after a threshold arc between the first member 102 and the second member 104 has been reached. Typically, the connection between the first member 102 and the second member 104 is relatively strong and does not decouple until force is intentionally applied to separate the two. The force is generally applied at the first section 204, and through the bending of the swab 100 on a container.

At the proximal end of the first member 102 may be the male connector 210. The male connector 210 may have a larger cross section than the groove 208 but smaller than the second section 206. The male connector 210 may be inserted into the second member 104 which will be shown below. The groove 208 and the male connector 210 may both be within the second member 104 when connected.

Figure 3A:
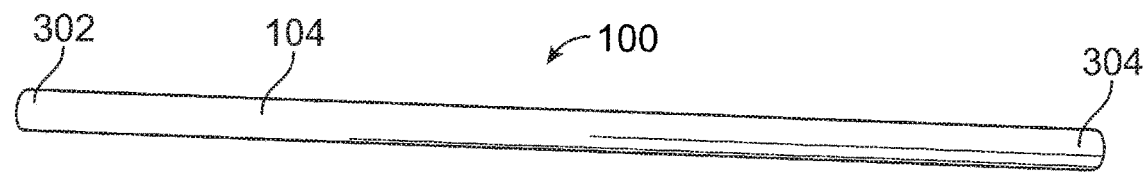
FIGS. 3A through 3D are schematic representations of an exemplary second member of the illustrative nasopharyngeal swab in accordance with one aspect of the present disclosure.

Referring to FIG. 3A, a schematic representation of the exemplary second member 104 of the illustrative nasopharyngeal swab 100 in accordance with one aspect of the present disclosure is provided. The second member 104, as discussed above, may be coupled or connected to the first member 102. The second member 104 may be made of similar or different materials as the first member 102. The second member 104 may include an elongated tubular structure. The structure may have a uniform cross sectional diameter throughout. The second member 104 may include a proximal end 302 and a distal end 304. The proximal end 302 may be near the practitioner while the distal end is near the patient and connected to the first member 102.

Figure 3B:
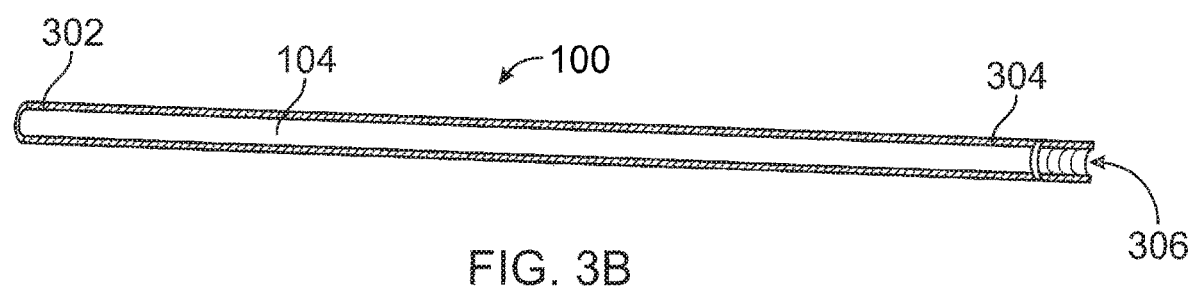

FIG. 3B is a schematic cross sectional representation of the exemplary second member 104 of the illustrative nasopharyngeal swab 100 in accordance with one aspect of the present disclosure. At the proximal end 302, the second member 104 may be solid, which may be extended until the distal end 304. The distal end 304 of the second member 104 of the nasopharyngeal swab 100 may include a female connector 306. The female connector 306 may have a diameter similar to or the same as the male connector 210 of the first member 102, Advantageously, this may allow for coupling of the two members 102 and 104. The female connector 306 may be an inlet and when coupled may contain a portion of the first member 102. The back portion of the male connector 210 may reached the back end of the female connector 306. In one example, the inlet is about two (2) mm to five (5) mm. The inlet may be larger or smaller depending on the materials used and an intended flexibility of the swab 100.

Figure 3C:
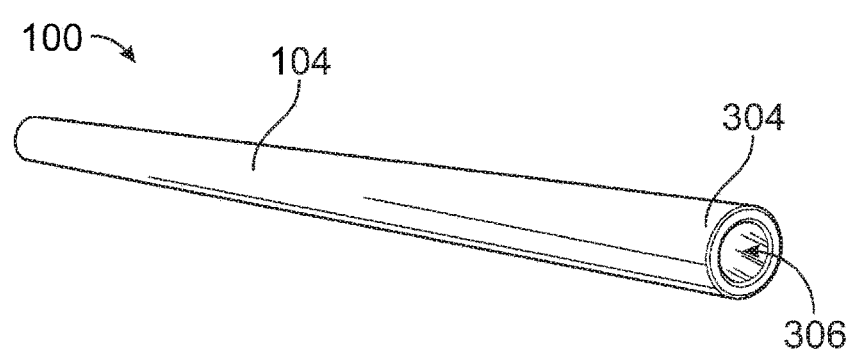

FIG. 3C is a side perspective view of the exemplary second member 104 of the illustrative nasopharyngeal swab 100 in accordance with one aspect of the present disclosure. The female connector 306 on the distal end 304 may be an inlet or aperture for the male connector 210 of the first member 102. The inlet may have a cross sectional size and distance of the combined groove 208 and male connector 210. A snug or tight fit may be achieved when pressure is applied to the members 202 and 204 of the nasopharyngeal swab 100 such that a small to regular lateral force would not dislodge the coupling.

Figure 3D:
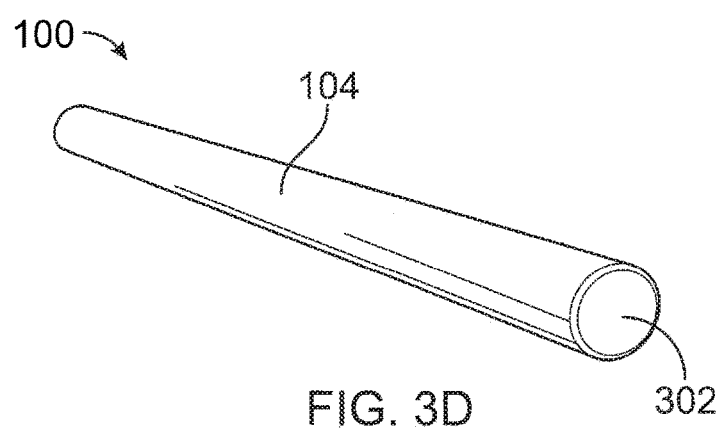

FIG. 3D is a side perspective view of the exemplary second member 104 of the illustrative nasopharyngeal swab 100 in accordance with one aspect of the present disclosure. The proximal end 302 may be closed. The cross sectional area between the proximal end 302 to the female connector 306 may be made of solid materials such that little bending occurs. This sturdiness may be used to form a handle on the second member 104. This handle would allow a practitioner to have control of the swab 100.

Figure 4:
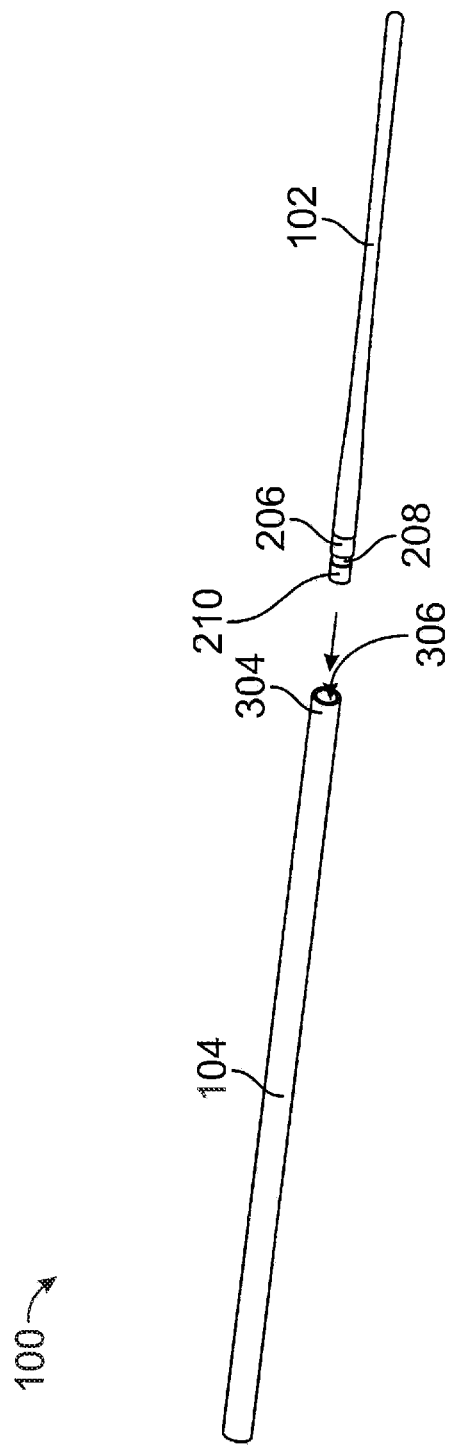
FIG. 4 is a schematic representation of an exemplary process for affixing the first member into the second member of the illustrative nasopharyngeal swab in accordance with one aspect of the present disclosure.

With reference to FIG. 4, a schematic representation of an exemplary process for affixing the first member 102 into the second member 104 of the illustrative nasopharyngeal swab 100 in accordance with one aspect of the present disclosure is provided. As previously described, the first member 102 may include a second section 206, groove 208 and a male connector 210. This in combination with the female connector 306 on the distal end 304 end of the second member 104 may be used to form a coupling.

Minimal force may be applied to fit the first member 102 into the second member 104 of the nasopharyngeal swab 100. Force may also be applied from the second member 104 to the first member 102, or vice versa. The second member 104 may be prevented from extending further onto the first member 102 through the second section 206 and the depth of the female connector 306. When connected, the groove 208 and the male connector 210 may be retained within the female connector 306. This fit may create a tight seal, however, it may be breakable when enough force is applied in a lateral direction on either or both ends of the nasopharyngeal swab 100. Typically, the first member 102 may be decoupled from the second member 104 when lateral force is applied to the first section 204 of the first member 102, which will be shown below.

Figure 5:
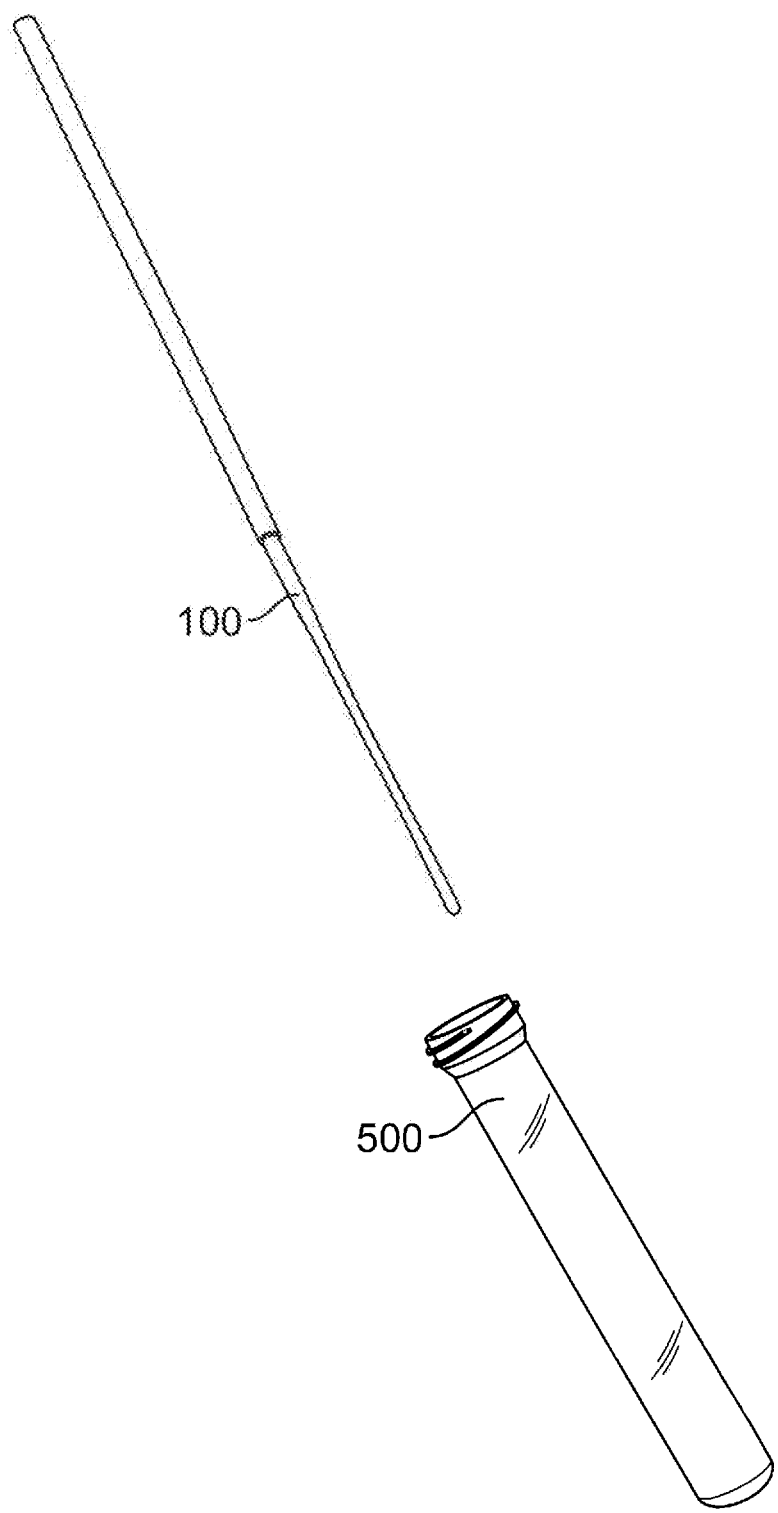
FIG. 5 is a schematic representation of an exemplary first procedure for securing a sample from the illustrative nasopharyngeal swab in accordance with one aspect of the present disclosure.

FIG. 5 is a schematic representation of an exemplary first procedure for securing a sample from the illustrative nasopharyngeal swab 100 in accordance with one aspect of the present disclosure. The nasopharyngeal swab 100 may be assembled through the first member 102 and second member 104 as described above. To collect a sample, the patient may be positioned with his or her face pointing upwards. The swab 100 may be inserted through a nasal cavity of the patient. The swab 100 may be placed at a point coinciding with an outer opening of an ear of the patient. In turn, the swab 100 may be rotated before being removed. Typically a container 500 may be ready for collecting the sample.

Figure 6:
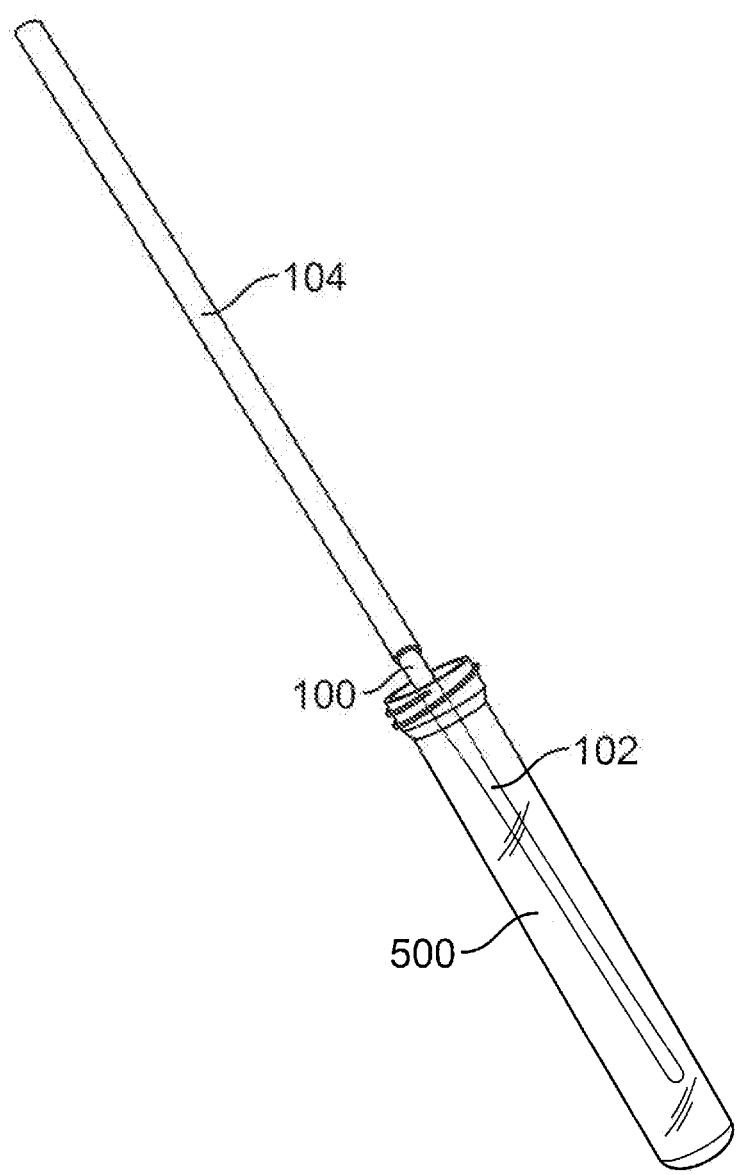
FIG. 6 is a schematic representation of an exemplary second procedure for securing the sample from the illustrative nasopharyngeal swab in accordance with one aspect of the present disclosure.

FIG. 6 is a schematic representation of an exemplary second procedure for securing the sample from the illustrative nasopharyngeal swab 100 in accordance with one aspect of the present disclosure. The procedure may include placing the nasopharyngeal swab 100 into the container 500. As shown, a portion of the first member 102 may be within the container 500. The other portion of the first member 102 may be outside the container 500 and connected to the second member 104.

Figure 7:
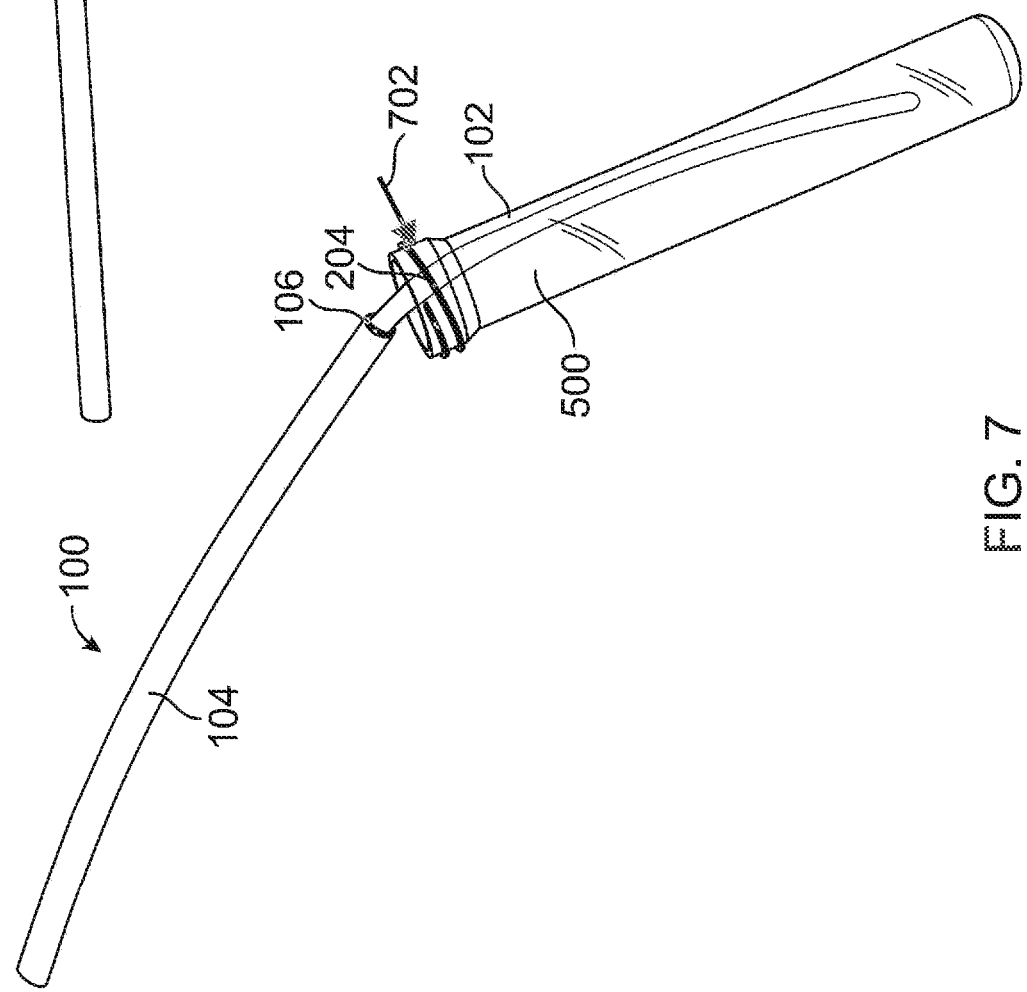
FIG. 7 is a schematic representation of an exemplary third procedure for securing the sample from the illustrative nasopharyngeal swab in accordance with one aspect of the present disclosure.

FIG. 7 is a schematic representation of an exemplary third procedure for securing the sample from the illustrative nasopharyngeal swab 100 in accordance with one aspect of the present disclosure. The second member 104 having the handle may be bent towards an outer edge of the container 500 with the tip of the first member 102 contacting a lower portion in the container 500. The connection point 106 between the members 102 and 104 may now be slipping or becoming loose.

As shown, force 702 may be applied by the container 500 when the second member 104 is bent backwards and the first member abuts an interior wall of the container 500. That is, the force 702 may be applied to the first section 204 of the first member 102 through the container when the second member 104 is arced. After reaching a threshold arc, the first member 102 and second member 104 may be decoupled. The force 702 to decouple the first member 102 from the second member 104 may typically be applied at or near a proximal portion of the first member 102.

Figure 8:
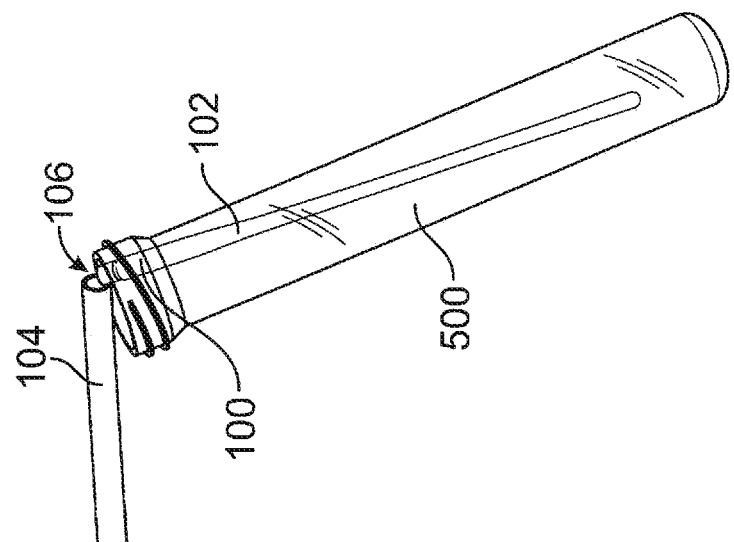
FIG. 8 is a schematic representation of an exemplary fourth procedure for securing the sample from the illustrative nasopharyngeal swab in accordance with one aspect of the present disclosure.

FIG. 8 is a schematic representation of an exemplary fourth procedure for securing the sample from the illustrative nasopharyngeal swab 100 in accordance with one aspect of the present disclosure. The bending between the members 102 and 104 may have now caused them to be separated at the connection point 106. The lateral force applied by bending the nasopharyngeal swab 100 may cause this break. The break generally occurs at a threshold arc between the first member 102 and second member 104.

Figure 9:
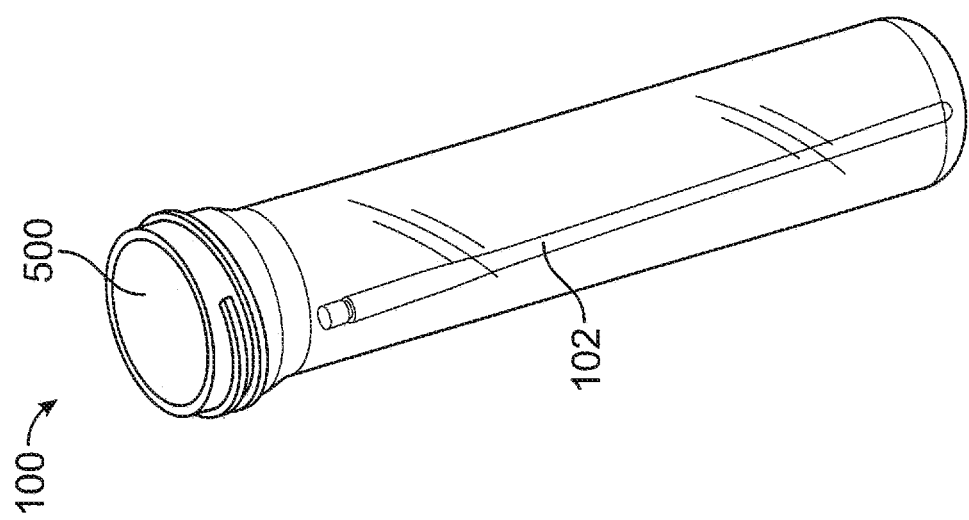
FIG. 9 is a schematic representation of an exemplary fifth procedure for securing the sample from the illustrative nasopharyngeal swab in accordance with one aspect of the present disclosure.

FIG. 9 is a schematic representation of an exemplary fifth procedure for securing the sample from the illustrative nasopharyngeal swab 100 in accordance with one aspect of the present disclosure. The first member 102 having the collected specimen has dropped into the container 500 after the break. That is, the first member 102 may have been decoupled from the second member 104.

Figure 10:
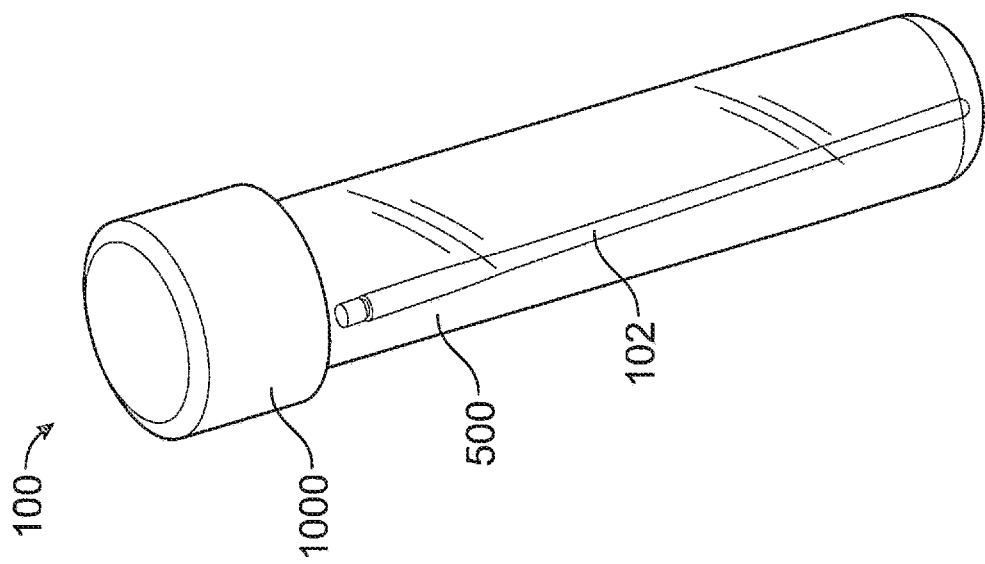
FIG. 10 is a schematic representation of an exemplary sixth procedure for securing the sample from the illustrative nasopharyngeal swab in accordance with one aspect of the present disclosure.

FIG. 10 is a schematic representation of an exemplary sixth procedure for securing the sample from the illustrative nasopharyngeal swab 100 in accordance with one aspect of the present disclosure. The first member 102 of the swab 100 has now been deposited into the container 500. A lid 1000 may be placed onto the container 500 to secure the specimen. The specimen within the container 500 may be thereafter analyzed.

The foregoing description is provided to enable any person skilled in the relevant art to practice the various embodiments described herein. Various modifications to these embodiments will be readily apparent to those skilled in the relevant art and generic principles defined herein may be applied to other embodiments. Thus, the claims are not intended to be limited to the embodiments shown and described herein, but are to be accorded the full scope consistent with the language of the claims, wherein reference to an element in the singular is not intended to mean "one and only one" unless specifically stated, but rather "one or more." All structural and functional equivalents to the elements of the various embodiments described throughout this disclosure that are known or later come to be known to those of ordinary skill in the relevant art are expressly incorporated herein by reference and intended to be encompassed by the claims. Moreover, nothing disclosed herein is intended to be dedicated to the public regardless of whether such disclosure is explicitly recited in the claims.

What is claimed is:

1. A swab comprising:
   a single piece first member having:
      a collection end at a distal portion of the first member;
      a first section at a proximal portion of the first member and having a larger cross-sectional area than the distal portion of the first member;
      a coupling structure connected to the first section at the proximal portion of the first member, the coupling structure comprising:
         a second section having a larger cross section than the first section;
         a male connector having a uniform circular centered cross section, having a length of two (2) mm to five (5) mm, and having a smaller cross section than the second section; and
         a groove between the male connector and the second section, the groove having a circular cross section that is smaller than the uniform circular centered cross section of the male connector; and
   a single piece second member having a handle at a proximal portion of the second member and a female connector at a distal portion of the second member, the female connector having a cylindrical inlet extending two (2) mm to five (5) mm into the distal portion of the second member;
   wherein the first member and second member are coupled together at a connection point with the uniform circular centered cross section of the male connector and the groove inserted into the cylindrical inlet of the female connector.

2. The swab of claim 1, wherein the first member is an elongated tubular structure.

3. The swab of claim 1, wherein the second member is an elongated tubular structure.

4. A nasal swab constructed to collect and release a biological sample comprising:
   a single piece first member having:
      a collection end at a distal portion of the first member;
      a first section at a proximal portion of the first member and having a larger cross-sectional area than the distal portion of the first member;
      a coupling structure connected to the first section at the proximal portion of the first member, the coupling structure comprising:
         a second section having a larger cross section than the first section;
         a male connector, wherein the male connector has a uniform circular centered cross section and wherein the male connecter has a smaller cross section than the second section; and
         a groove between the male connector and the second section, the groove having a circular cross section that is smaller than the uniform circular centered cross section of the male connector; and
   a single piece second member having a handle at a proximal portion of the second member and a female connector at a distal portion of the second member, the female connector having a cylindrical inlet extending into the distal portion of the second member, wherein the first member and second member are coupled together at a connection point with the uniform circular centered cross section of the male connector and the groove inserted into the cylindrical inlet of the female connector.

5. The nasal swab constructed to collect and release the biological sample of claim 4, wherein the second member is an elongated tubular structure.

6. The nasal swab constructed to collect and release the biological sample of claim 4, wherein the first section of the first member is flat.

7. The nasal swab constructed to collect and release the biological sample of claim 4, wherein the cylindrical inlet of the female connector is two (2) mm to five (5) mm long.

* * * * *